United States Patent
Soehren et al.

(10) Patent No.: US 6,522,266 B1
(45) Date of Patent: Feb. 18, 2003

(54) NAVIGATION SYSTEM, METHOD AND SOFTWARE FOR FOOT TRAVEL

(75) Inventors: Wayne A. Soehren, Wayzata, MN (US); Charles T. Bye, Eden Prairie, MN (US); Charles L. Keyes, Forest Lake, MN (US)

(73) Assignee: Honeywell, Inc., Minneapolis, MN (US)

( * ) Notice: Subject to any disclaimer, the term of this patent is extended or adjusted under 35 U.S.C. 154(b) by 0 days.

(21) Appl. No.: 09/572,238

(22) Filed: May 17, 2000

(51) Int. Cl.[7] .............................................. G08G 1/123
(52) U.S. Cl. ........................ 340/988; 600/595; 702/160
(58) Field of Search ...................... 340/988; 73/178 R; 377/24.2, 39; 482/3, 8, 74; 600/595; 702/97, 160

(56) References Cited

U.S. PATENT DOCUMENTS

| | | | |
|---|---|---|---|
| 3,635,399 A | 1/1972 | Dahlquist et al. ........... 235/105 |
| 3,797,010 A | 3/1974 | Adler et al. ................. 340/323 |
| 3,901,086 A | 8/1975 | Griffiths et al. ............... 73/490 |
| 4,053,755 A | 10/1977 | Sherrill ........................ 364/561 |
| 4,149,417 A | 4/1979 | Griffiths et al. ............... 73/490 |
| 4,220,996 A | * 9/1980 | Searcy ....................... 702/160 |
| 4,409,992 A | 10/1983 | Sidorenko et al. .......... 128/782 |
| 4,991,126 A | 2/1991 | Reiter ......................... 364/561 |
| 5,117,301 A | 5/1992 | Tsumura ..................... 359/154 |
| 5,117,444 A | 5/1992 | Sutton et al. ............... 377/24.2 |
| 5,367,458 A | 11/1994 | Roberts et al. ......... 364/424.02 |
| 5,485,402 A | 1/1996 | Smith et al. ................. 364/566 |
| 5,583,776 A | 12/1996 | Levi et al. ................... 364/450 |
| 5,760,737 A | 6/1998 | Brenner ....................... 342/357 |
| 5,955,667 A | 9/1999 | Fyfe |
| 6,064,942 A | * 5/2000 | Johnson et al. ............. 701/213 |
| 6,122,960 A | * 9/2000 | Hutchings et al. ............ 73/493 |
| 6,132,391 A | * 10/2000 | Onari et al. ................. 600/595 |
| 6,243,660 B1 | * 6/2001 | Hsu et al. .................... 702/160 |
| 6,298,314 B1 | * 10/2001 | Blackadar et al. .......... 702/178 |
| 6,301,964 B1 | * 10/2001 | Fyfe et al. ..................... 73/510 |

FOREIGN PATENT DOCUMENTS

| | | |
|---|---|---|
| DE | 19946212 | 4/2000 |
| FR | 2670004 A | 6/1992 |
| WO | 9306779 A | 4/1993 |

OTHER PUBLICATIONS

Aminian K et al: "Estimation of Speed and Incline of Walking Using Neural Network" IEEE Transactions on Instrumentation and Measurement, IEEE Inc. New York, US, vol. 44, No. 3, Jun. 1, 1995, pp. 743–746, xp000527554, ISSN: 0018–9456.

(List continued on next page.)

Primary Examiner—John A. Tweel
(74) Attorney, Agent, or Firm—Schwegman, Lundberg, Woessner & Kluth PA

(57) ABSTRACT

A navigation system for mounting on a human. The navigation system includes one or more motion sensors for sensing motion of the human and outputting one or more corresponding motion signals. An inertial processing unit coupled to one or more of motion sensors determines a first position estimate based on one or more of the corresponding signals from the motion sensors. A distance traveled is determined by a motion classifier coupled to one or more of the motion sensors, where the distance estimate is based on one or more of the corresponding motion signals processed in one or more motion models. A Kalman filter is also integrated into the system, where the Kalman filter receives the first position estimate and the distance estimate and provides corrective feedback signals to the inertial processor for the first position estimate. In an additional embodiment, input from a position indicator, such as a GPS, provides a third position estimate, and where the Kalman filter provides corrections to the first position estimate, the distance estimate and parameters of the motion model being used.

29 Claims, 9 Drawing Sheets

OTHER PUBLICATIONS

In: *Kalman Filtering: Theory and Application*, Sorenson, H. W., (ed.), IEEE Press, New York,, 1–2, (1985).

Berg, R.F., "Estimation and Prediction for Maneuvering Target Trajectories", *IEEE Transactions on Automatic Control, AC–28*, 303–313, (Mar. 1983).

Bowditch, N., "American Practical Navigator An Epitome of Navigation", *American Practical Navigator An Epitome of Navigation, Corrected Print–1966*, 248–250, (1966).

Cipra, B., "Engineers look to Kalman filtering for guidance", *Society for Industrial and Applied Mathematics News, 26*, found at web address: http://www.cs.unc.edu/~welch/siam_$_{13}$ cipra.html, 1–4, (Aug. 1993).

Evans, M., "Global Positioning Systems/Inertial Navigation Systems Integration Project", *http://wwwcrasys.anu.edu.au/admin/annualReports/1996–96/7–10.html*, 1–3, (Nov. 1996).

Langley, R.B., "The Integrity of GPS", *http://www.gpsworld.com/0699/0699innov.html*, 1–9, (c.1999).

Leibundgut, B.G., et al., "Application of Kalman Filtering to Demographic Models", *IEEE Transactions on Automatic Control, AC–28*, 427–434, (Mar. 1983).

Levy, L.J., "The Kalman Filter: Navigation's Integration Workhorse", *http://www.gpsworld.com/columns/0997Innov/0997kalman.htm*, 1–12, (c.1999).

Margaria, R., "Biomechanics of Human Iocomotion", *Biomechanics and Energetics of Muscular Exercise In*, Clarendon Press, 106–124, (1976).

Maybeck, P.S., "Stochastic Models, Estimation, and Control", *Stochastic Models, Estimation, and Control, 1*, Chapter 1–Introduction, Academic Press, Inc., 1–16, (c.1979).

Meijer, G.A., et al., "Methods to Assess Physical Activity with Special Reference to Motion Sensors and Accelerometers", *IEEE Transactions on Biomedical Engineering, 38*, 221–229, (Mar. 1991).

Sorenson, H.W., "Least–squares estimation: from Gauss to Kalman", *IEEE Spectrum, 7*, 7–15, (Jul. 1970).

Van Diggelen, F., "GPS Accuracy: Lies, Damn Lies, and Statistics", *http://www.gpsworld.com/columns/9805innov.html*, 1–7, (c.1998).

\* cited by examiner

NAVIGATION SYSTEM, METHOD AND SOFTWARE FOR FOOT TRAVEL

TECHNICAL FIELD

The present invention relates to navigation systems, and in particular the invention relates to personal navigation systems.

BACKGROUND OF THE INVENTION

Reliable navigation systems have always been essential for estimating both distance traveled and position. Some of the earliest type of navigation systems relied upon navigation by stars, or celestial navigation. Prior to the development of celestial navigation, navigation was done by "deduced" (or "dead") reckoning. In dead-reckoning, the navigator finds his position by measuring the course and distance he has moved from some known point. Starting from a known point the navigator measures out his course and distance from that point. Each ending position would be the starting point for the course-and-distance measurement.

In order for this method to work, the navigator needs a way to measure his course, and a way to measure the distance moved. Course is measured by a magnetic compass. Distance is determined by a time and speed calculation: the navigator multiplied the speed of travel by the time traveled to get the distance. This navigation system, however, is highly prone to errors, which when compounded can lead to highly inaccurate position and distance estimates.

An example of a more advanced navigation system is an inertial navigation system (INS). The basic INS consists of gyroscopes, accelerometers, a navigation computer, and a clock. Gyroscopes are instruments that sense angular rate. They are used to give the orientation of an object (for example: angles of roll, pitch, and yaw of an airplane). Accelerometers sense a linear change in rate (acceleration) along a given axis.

In a typical INS, there are three mutually orthogonal gyroscopes and three mutually orthogonal accelerometers. This accelerometer configuration will give three orthogonal acceleration components which can be vectorially summed. Combining the gyroscope-sensed orientation information with the summed accelerometer outputs yields the INS's total acceleration in 3D space. At each time-step of the system's clock, the navigation computer time integrates this quantity once to get the body's velocity vector. The velocity vector is then time integrated, yielding the position vector. These steps are continuously iterated throughout the navigation process.

Global Positioning System (GPS) is one of the most recent developments in navigation technology. GPS provides highly accurate estimates of position and distance traveled. GPS uses satellites to transmit signals to receivers on the ground. Each GPS satellite transmits data that indicates its location and the current time. All GPS satellites synchronize operations so that these repeating signals are transmitted at the same instant. The signals, moving at the speed of light, arrive at a GPS receiver at slightly different times because some satellites are farther away than others. The distance to the GPS satellites can be determined by estimating the amount of time it takes for their signals to reach the receiver. When the receiver estimates the distance to at least four GPS satellites, it can calculate its position in three dimensions.

When available, positioning aids such as GPS control navigation error growth. GPS receivers, however, require an unobstructed view of the sky, so they are used only outdoors and they often do not perform well within forested areas or near tall buildings. In these situations, an individual using a GPS is without an estimate of both distance traveled and position. Therefore, a need exists for a system that integrates the best navigation features of known navigation techniques to provide an individual with estimates of position and distance traveled, regardless of where they might travel.

SUMMARY OF THE INVENTION

The present invention provides solutions to the above-identified problems. In an exemplary embodiment, the present invention integrates traditional inertial navigation and independent measurements of distance traveled to achieve optimal geolocation performance in the absence of GPS or other radio-frequency positioning aids. The present invention also integrates the use of GPS to control navigation error growth. However, when GPS signals are jammed or unavailable, the present system still provides a useful level of navigation performance.

The expected performance characteristics of reasonably priced INS sensors, in particular the gyroscopes, have little practical value for long-term navigation applications (>60 seconds) using inertial navigation algorithms alone. Dead reckoning techniques provide a better long-term solution; however, for best performance, these techniques require motion that is predictable (i.e., nearly constant step size and in a fixed direction relative to body orientation). Unusual motions (relative to walking) such as sidestepping are not handled and can cause significant errors if the unusual motion is used for an extended period of time. Integrating traditional inertial navigation and independent measurements of distance traveled offers a solution to achieve optimal geolocation performance in the absence of GPS or other radio-frequency positioning aids.

In one exemplary embodiment, the invention provides a navigation system for mounting on a human. The navigation system includes one or more motion sensors for sensing motion of the human and outputting one or more corresponding motion signals. An inertial processing unit coupled to one or more of motion sensors determines a first position estimate based on one or more of the corresponding signals from the motion sensors. A distance traveled is determined by a motion classifier coupled to one or more of the motion sensors, where the distance estimate is based on one or more of the corresponding motion signals. In one embodiment, the motion classifier includes a step-distance model and uses the step-distance model with the motion signals to determine the distance estimate.

A Kalman filter is also integrated into the system, where the Kalman filter receives the first position estimate and the distance estimate and provides corrective feedback signals to the inertial processor for the first position estimate. In one embodiment, the Kalman filter determines the corrective feedback signals based on the first position estimate and the distance estimate and past and present values of the motion signals. In an additional embodiment, input from a position indicator, such as a GPS, provides a third position estimate, and where the Kalman filter provides corrections to the first position estimate and the distance estimate using the third position estimate. The Kalman filter also provides corrections (e.g., modifications) to parameters of the motion model based on the errors in the distance estimate. In one embodiment, the modifications to the model parameters are specific to one or more humans.

The present invention also provides for a motion classification system. The motion classification system includes first sensors coupled to a processor to provide a first type of motion information, and second sensors coupled to the processor to provide a second type of motion information. In one exemplary embodiment, the first sensors are a triad of inertial gyroscopes and the second sensors are a triad of accelerometers. A neural-network is then employed to analyze the first and second types of motion information to identify a type of human motion. The neural-network is used to identify the type of human motion as either walking forward, walking backwards, running, walking down or up an incline, walking up or down stairs, walking sideways, crawling, turning left, turning right, stationary, or unclassifiable. Once identified, motion models specific for the motion type are used to estimate a distance traveled. The distance traveled estimate is then used with the navigation system for mounting on the human to provide distance traveled and location information as described above.

DETAILED DESCRIPTION

Figure 1:
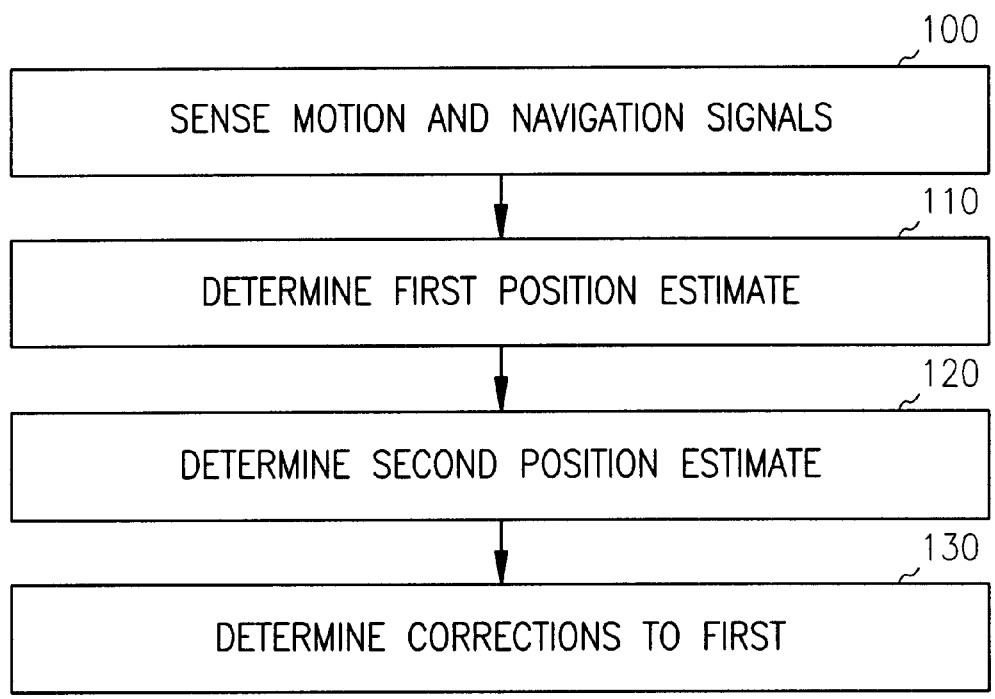
FIG. 1 shows an exemplary method of the present invention.

An exemplary navigation/geolocation system for an individual is disclosed. The exemplary system provides enhanced navigation and position estimates for users traveling on foot. The exemplary system uses inertial navigation information gathered from the individual, a motion algorithm which identifies the motion type of the individual (e.g., walking) along with Kalman filtering to estimate travel distance and position. More particularly, the exemplary system compares the data from the motion algorithm and an inertial navigation processing unit using the Kalman filter to determine reliable travel distance and position information. This information is then used to estimate the individual's position and distance traveled. In one embodiment, the present system is incorporated into a self-contained apparatus, which is worn by the user.

The exemplary system can also incorporate information gathered from a global positioning system (GPS) or other radio frequency positioning aids. GPS provides superior position and distance traveled information as compared to either the inertial navigation processing unit or the motion model algorithm. The exemplary system uses the additional GPS input to correct estimates of distance and position from the inertial navigation processing unit and modify the motion model parameters to maintain optimal performance.

Small low-cost inertial sensors (i.e gyroscopes and accelerometers) make the standard strapdown inertial navigation algorithms useful for only short periods of time (<60 seconds). Conventional dead-reckoning techniques, which can provide better navigation performance than inertial navigation over longer periods of time, require the individual to move predictably (i.e., nearly constant step size and in a fixed direction relative to body orientation) for accurate geolocation and navigation information. Unfortunately, the user does not always move in a predictable manner and unusual motions (relative to walking), such as sidestepping, crawling, running, climbing, etc. are not correctly interpreted by conventional dead reckoning techniques. As a result, significant errors accumulate, eroding the accuracy of the conventional dead-reckoning systems.

GPS is one possible means of providing accurate geolocation and distance traveled information. However, GPS, and other RF location aids, are not always available because of satellite or transmitter outages, obstacles to radio-signal transmissions, and so forth. This leads to an unacceptable situation in which the individual's position and distance traveled are not accurately accounted for due to the shortcomings of using either the inertial navigation or traditional dead-reckoning systems alone.

An advantage of the exemplary system is the ability to continue to provide accurate estimates of geolocation and distance traveled even when GPS, or other RF positioning aids, are not available. The exemplary system solves these, and other, problems by integrating inertial navigation and motion-model algorithms using a Kalman filter for estimating the geolocation of the user in the absence of GPS or other radio-frequency position aids. The exemplary system also allows for user-specific enhancements and changes to the motion classification model when GPS positioning is used.

FIG. 1 shows an exemplary method of estimating foot-travel position according to the present invention. At 100, one or more motion signals are sensed through one or more motion sensors, and one or more navigation signals are sensed through one or more navigation sensors for providing motion data about a user. In one embodiment, the one or more motion sensors include accelerometers and gyroscopes as are used in inertial navigation systems. In an additional embodiment, the one or more motion sensors can further include magnetic sensors and step sensors as are used in dead reckoning systems.

At 110, a first position estimate for the foot-travel position is determined from the one or more motion signals. In one embodiment, the first position estimate includes an estimate of the individual's geolocation, along with the distance traveled, as derived from signals from the accelerometers and gyroscopes as used in inertial navigation systems.

At 120, a second position estimate for the foot-travel position is determined from the one or more navigation signals. In one embodiment, the second position estimate includes an estimate of the individual's geolocation, along with the distance traveled, from the magnetic sensors and step sensors as are used in dead reckoning systems.

At 130, the first position estimate and the second position estimate are then integrated to determine corrections to the first position estimate. In one embodiment, the first and the second position estimates of foot-travel are determined by using past and present values of either the navigation signals or the motion signals. For example, a Kalman filter is used to provide the corrections to the first position estimate. The first estimate then represents an optimal system solution. Either the first or the second position estimate of geolocation and distance traveled is then displayed in a human-perceptible form, such as on a display terminal.

Figure 2:
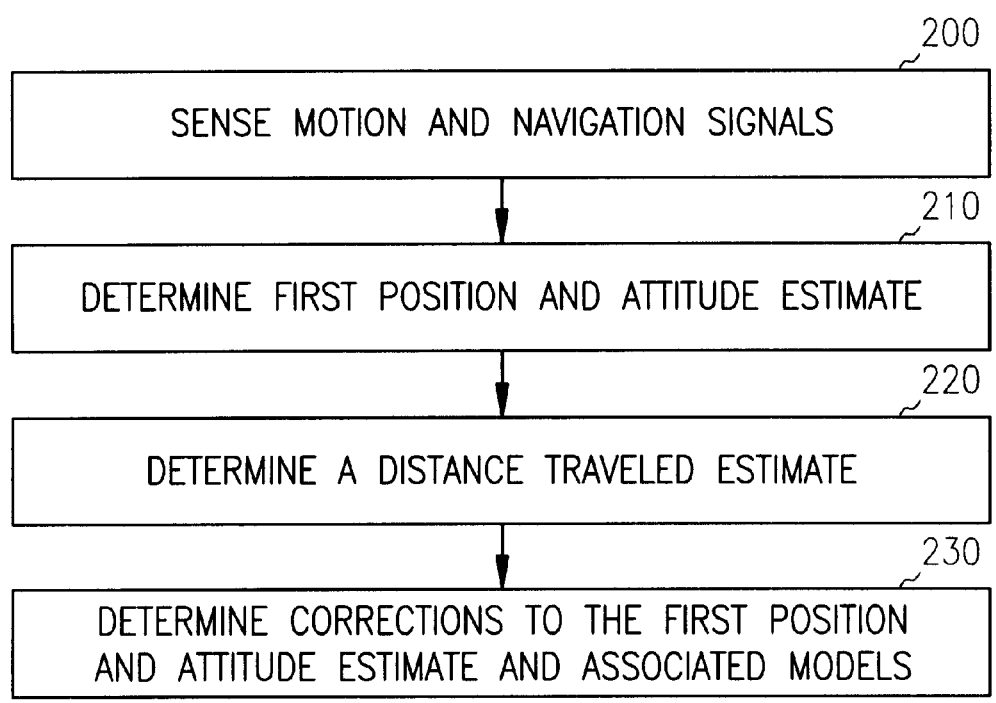
FIG. 2 shows an exemplary method of the present invention.

FIG. 2 shows a second exemplary method of estimating foot-travel position according to the present invention. At 200, one or more motion signals are sensed through one or more motion sensors, and one or more navigation signals are sensed through one or more navigation sensors for providing motion data about a user. In one embodiment, the one or more motion sensors include accelerometers, gyroscopes, and magnetic sensors as are used in inertial navigation and/or dead reckoning systems.

At 210, a first position and attitude estimate for the foot-travel position is determined from the one or more motion signals. In one embodiment, the first position estimate includes an estimate of the individual's geolocation and attitude, along with the distance traveled, derived from signals from the accelerometers and gyroscopes used in inertial navigation system.

At 220, a distance traveled estimate for the user is determined from the one or more navigation signals. In one embodiment, determining the distance traveled estimate is from a motion model for the type of motion being performed and an estimate of step frequency.

At 230, the first position and attitude estimate, the distance traveled estimate, and heading determined from the magnetic sensors are then integrated to determine corrections to the first position and attitude estimate. In one embodiment, the distance traveled and magnetic heading are compared to equivalent values generated from the first position and attitude estimates to generate Kalman filter measurements. The Kalman filter is used to provide the corrections to the first position and attitude estimate. The first estimate then represents the optimal system solution. The first position estimate of geolocation and distance traveled is then displayed in a human-perceptible form, such as on a display terminal.

Figure 3:
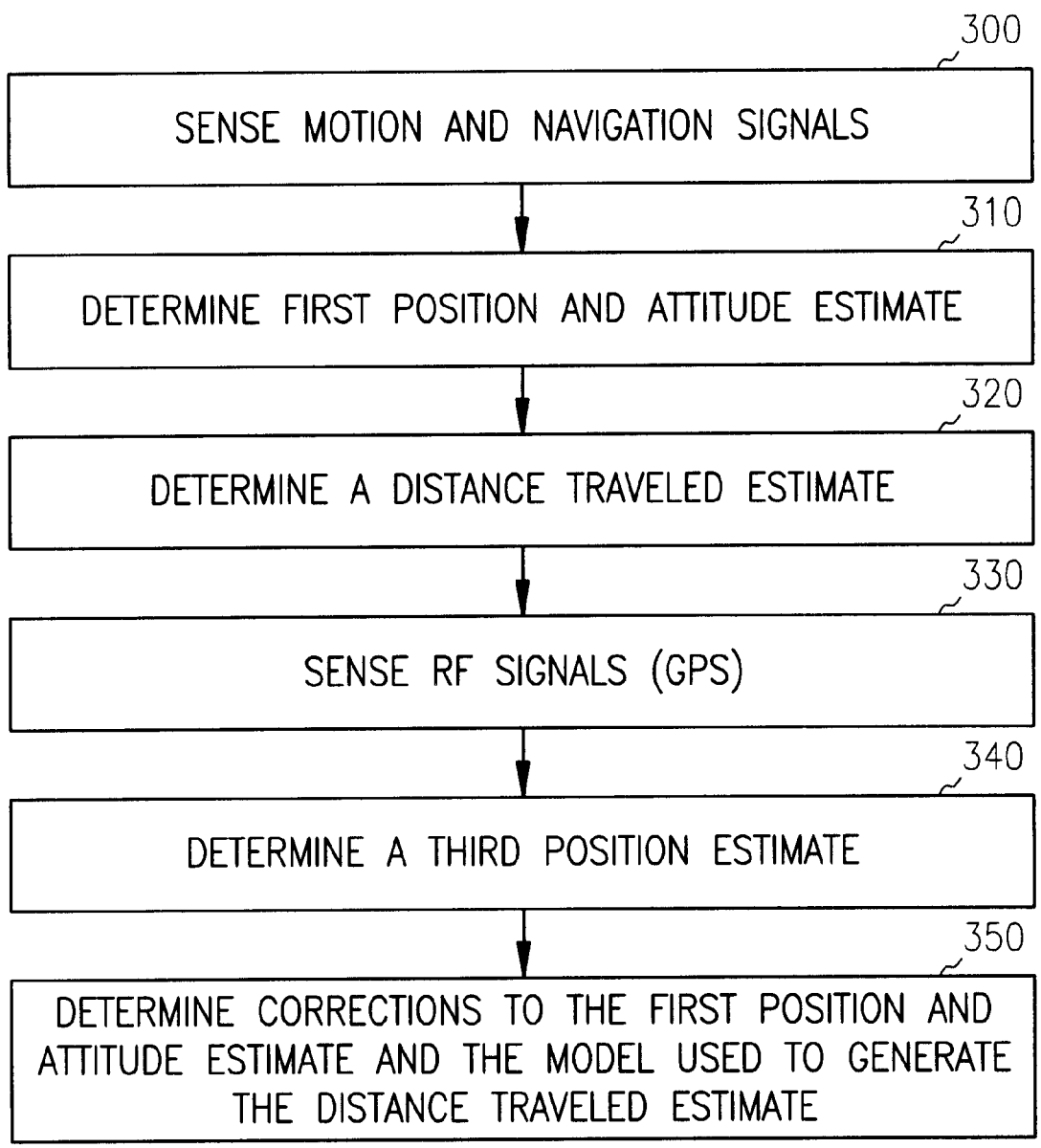
FIG. 3 shows an exemplary method of the present invention.

FIG. 3 shows an additional exemplary method of estimating foot-travel position according to the present invention. At 300, one or more motion signals are sensed through one or more motion sensors, and one or more navigation signals are sensed through one or more navigation sensors for providing motion data about a user. In one embodiment, the one or more motion sensors include accelerometers, gyroscopes, and magnetic sensors as are used in inertial navigation and/or dead reckoning systems.

At 310, a first position and attitude estimate for the foot-travel position is determined from the one or more motion signals. In one embodiment, the first position estimate includes an estimate of the individual's geolocation and attitude, along with the distance traveled as derived from an inertial navigation system.

At 320, a distance traveled estimate for the user is determined from the one or more navigation signals. In one example, this is determined from determining both the motion class of the step being taken and the frequency of the steps.

At 330 one or more RF signals are sensed through one or more RF antennas. In one embodiment, the RF signals emanate from the GPS satellite constellation.

At 340, a third position estimate is determined from a position indicator. In one embodiment, the position indicator is a GPS receiver.

At 350, differences between the first position estimate and the third position estimate are then taken and used by a Kalman filter to determine and provide corrections to the first position and attitude estimate and the model used to generate the distance traveled estimate at 320. In one embodiment, a difference between the first position estimate and the third position estimate is taken and used by the Kalman filter to identify errors in the first position estimate.

The parameters of the motion model (used to estimate distance traveled) are then modified based on the errors in the first position estimate. The first estimate then represents the optimal system solution. The first and/or the third position estimate of geolocation and distance traveled is then displayed in a human-perceptible form, such as on a display terminal.

Figure 4:
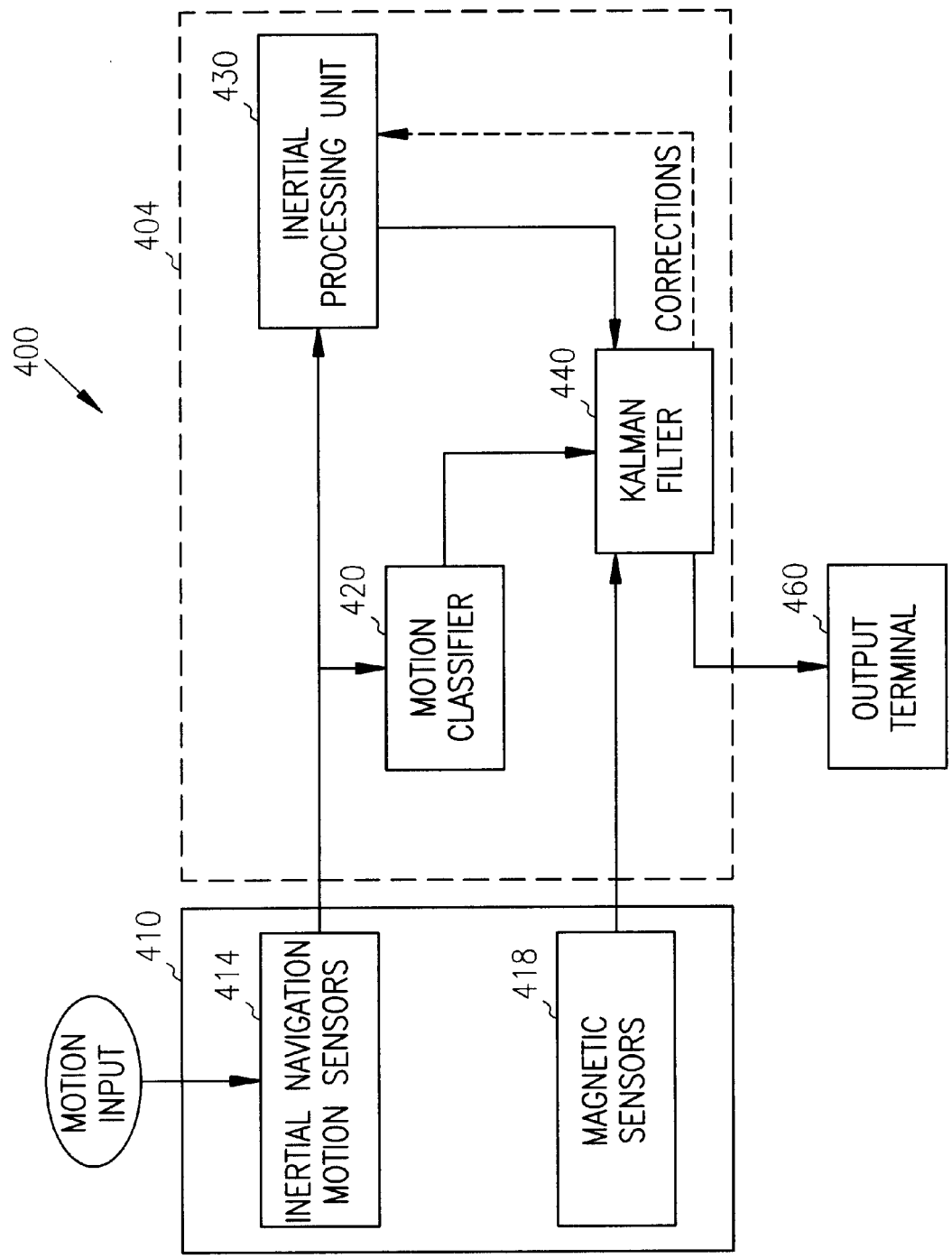
FIG. 4 shows a system of the present invention.

FIG. 4 shows an exemplary navigation system 400 for mounting on a human according to the present invention. The system 400 includes a computer or processor 404 having one or more motion (or navigation) sensors 410 for sensing motion of the human and outputting one or more corresponding motion (or navigation) signals. In one example, the sensors 410 include an inertial navigation motion sensor 414 and magnetic sensors 418.

The system 400 further includes a motion classifier 420, where the motion classifier 420 is coupled to one or more of the navigation sensors and the motion sensors 410. The motion classifier 420 uses the signals from the sensors 410 to determine a distance estimate. The motion classifier 420 implements an algorithm, which models step distance. In the exemplary system, a linear relationship between step size and walking speed that is tailored to the individual user is used. One example of this linear relationship is found in *Biomechanics and Energetics of Muscular Exercise*, by Rodolfo Margaria (Chapter 3, pages 107–124. Oxford: Clarendon Press 1976)

In one example, the magnetic sensors 418 and the accelerometers of the inertial navigation sensors 414 are used to estimate step frequency and direction. In one embodiment, the magnetic sensors 418 consist of three magnetic sensors mounted orthogonally. Distance traveled and direction of travel are determined using both the frequency of step (i.e., number of steps counted per unit time) along with the heading of the steps. The motion classifier 420 then takes the estimated step length, the frequency of steps, and the motion direction for the steps, and calculates the distance traveled estimate.

The system 400 further includes an inertial processing unit 430 coupled to the motion/navigation sensors 410. The inertial processing unit 430 uses the signals from the one or more navigation sensors and the motion sensors 410 to determine the first position estimate. The inertial navigation sensors 414 includes a triad of accelerometers and a triad of gyroscopes that provide the navigation signals of orthogonal movement and direction in three dimensions to the inertial processing unit 430. The inertial processing unit 430 then processes the signals according to known techniques to provide the first position estimate and the attitude estimate. The first position and attitude estimates and distance traveled estimate are then used in determining corrections that are applied back to the first position and attitude estimates.

In the exemplary system 400, as motion and direction are sensed by the magnetic sensors 418 and the inertial navigation sensors 414 (e.g., when the individual moves) samples of data are taken from the sensors at a predetermined rate. In one embodiment, the sensors of the inertial navigation sensors 414 are sampled at a rate of 100 samples/second, where measurements are taken on the rates on the three axes and the acceleration on the three axes. The sampled data is then supplied to both the inertial processing unit 430 and the motion classifier 420. The inertial processing unit 430 processes the data with a navigation algorithm to determine the first position estimate, which can include both direction and heading and the distance moved in that direction.

In the exemplary system, data samples supplied to the motion classifier 420 are analyzed for artifacts indicative of motion, such as peaks exceeding predetermined thresholds in the acceleration data indicating movement (e.g., a step) of the individual. As an artifact meeting the requirement to indicate movement, the time the artifact occurred is recorded and saved in the motion classifier 420, while the data continues to be analyzed for additional artifacts. Based on additional artifacts, along with acceleration information, a rate at which the individual is stepping is estimated by the motion classifier 420. The step period (i.e., time between each step) is used by the motion classifier to estimate the step distance based on the classification of the motion by the motion classifier 420.

The system 400 also includes a Kalman filter 440 which receives and integrates the first position estimate and the distance traveled estimate to determine corrective feedback signals using the past and present values of the navigation signals. In one embodiment, the Kalman filter 440 allows for poor distance estimates to be identified and ignored through Kalman filter residual testing, thus improving the overall solution. The residual test provides a reasonableness comparison between the solution based on the distance estimate (and heading angle) and the solution computed using the inertial navigation equations. This allows the algorithm of the exemplary system to combine the best features of dead-reckoning and inertial navigation in the absence of GPS or other RF aids, resulting in positioning performance exceeding that achieved with either method alone.

The Kalman filter 440 estimates corrective feedback signals and provides the corrective signals to the inertial processing unit 430 to correct the navigation error and the first position estimate. In one embodiment, the data from the motion classifier 420 and the inertial processing unit 430 are buffered and samples of the data are sent to the Kalman filter 440. This information provides a measure of the length of each step and the time the step was taken. A total distance traveled is estimated by adding the distances from the estimates of each step length by the inertial processing unit 430. The total distance traveled is also estimated through the use of the motion classifier 420 from the rate and number of steps taken by the individual. The Kalman filter 440 receives the distance-traveled estimates from the inertial processing unit 430 and the motion classifier 420 and uses the difference between the two values to calculate an error. The error between these two estimates is taken by the Kalman filter 440 and this value is input as a measurement into the Kalman filter 440 for determining the error corrections for the first position estimate.

A simple case to visualize is a sidestep. The motion model assumes that the heading given by the magnetic sensors is the direction of travel. However, the actual direction is 90 degrees off from the heading. The inertial navigation sensors sense acceleration in the sideways direction, enabling the inertial processing unit 430 to accurately estimate the change in position corresponding to the sidestep. The difference between the motion model solution and the inertial solution is detected in the residual test, and the motion model input to the Kalman filter 440 would be ignored. In a conventional dead-reckoning system, the error in the assumed direction of travel is difficult to detect, leading to error buildup when normal walking patterns are not followed. So, based on models of the inertial sensors in the Kalman filter and the motion classification from the motion classifier 420, the Kalman filter 440 estimates an error in the measurements made by the sensors of the inertial navigation sensors 414 and makes corrections to the standard navigation set. (In other words, the Kalman filter 440 modifies the results of the inertial navigation position and distance traveled estimate resulting from the inertial navigation sensors 414). Navigation information (e.g., the first position estimate and the distance estimate) is then provided by the processor 404 through an output terminal 460 in human perceptible form.

In an additional embodiment, the present system uses the Kalman filter 440 in a blended inertial navigation system. In the blended inertial navigation system, the magnetic heading derived from the magnetic sensors 418 is compared and integrated with the heading as derived from the inertial processing unit 430. The difference between magnetic heading and the heading derived from the inertial processing unit 430 becomes another measurement to the Kalman filter 440. The Kalman filter 440 uses this measurement to correct errors in either the magnetic sensors or in the heading derived from the inertial navigation sensors 414 (e.g., from the gyroscopes).

For example, where pairs of steps are detected not only are the step distances sent to the Kalman filter 440, but also the step directions so that the X-, Y- and Z-coordinate frames of the step direction can be determined. In the exemplary system, the heading solution derived by the Kalman filter is then taken as a best-estimate heading, where a heading that is half way between the heading of the two steps is used to estimate the direction of the sensed motion. Thus, this additional embodiment does not use a pure magnetic heading, but rather uses a heading derived from all available sensors.

In an additional embodiment, a dead-reckoning system (having a magnetometer and accelerometer) could replace the magnetic sensor 418 and the motion classifier 420 of FIG. 4. The dead-reckoning system would provide a second position estimate based on both sensed heading and step frequency. In one embodiment, a solid-state "strapdown" magnetometer (consisting of three flux sensors mounted orthogonally) could be used, where a three-axis accelerometer set is used to resolve the magnetic fields into a heading angle. A flux gate type magnetometer could also be used. The first position estimate provided by the inertial processing unit 430 and the dead-reckoning system are then supplied to the Kalman filter, which could supply correction feedback to both the first and second position estimates.

Figure 5:
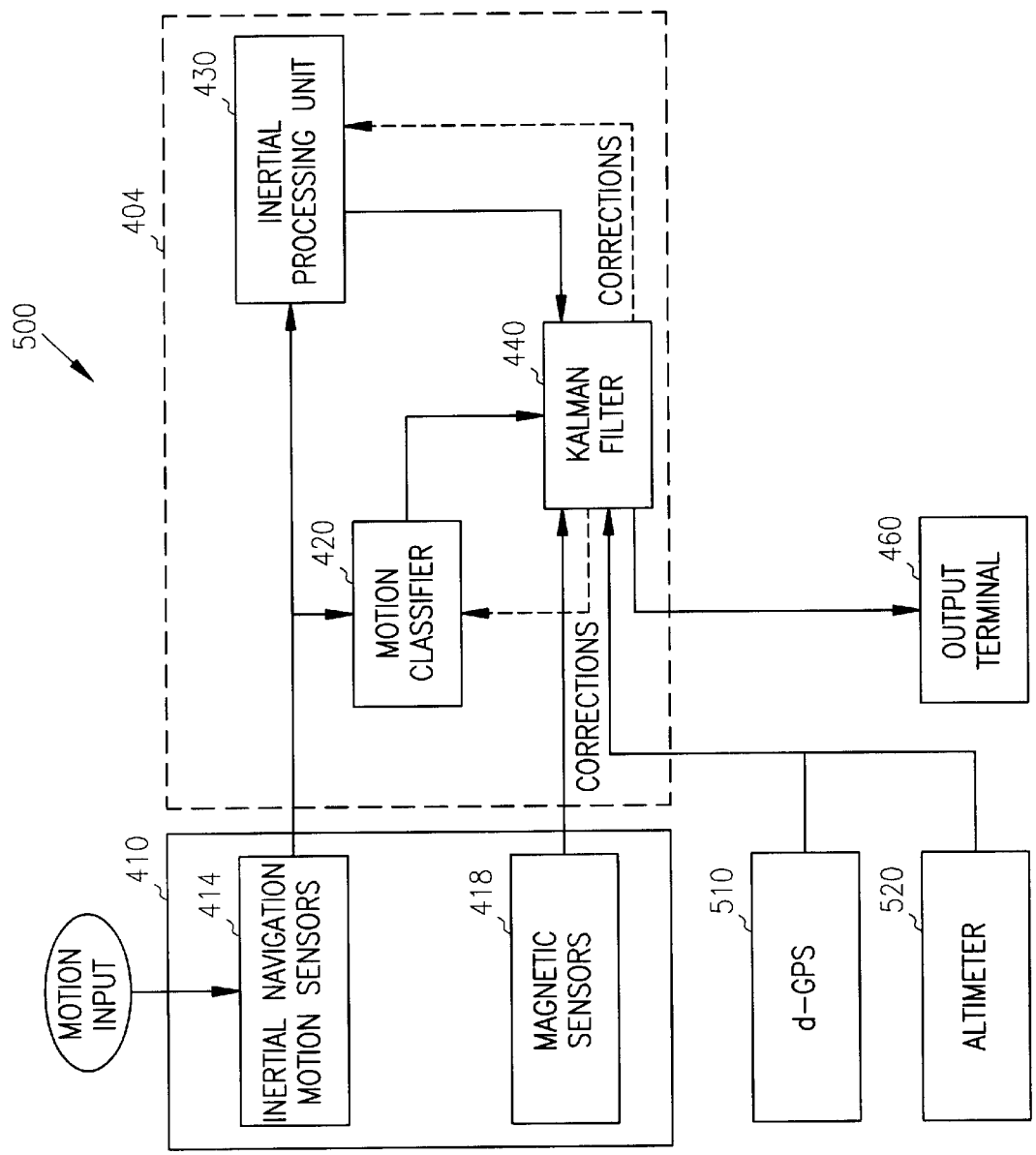
FIG. 5 shows a system of the present invention.

FIG. 5 shows an exemplary system 500 according to the present invention. The system 500 includes components similar to those in system 400, but system 500 further includes one or more additional position-aiding indicators coupled to a third input of the system 400 to supply a third position estimate to the processor 404 of the system 500. Exemplary position-aiding indicators include a global positioning receiver/processor of a global positioning system (GPS), and/or an altimeter. In one embodiment, global positioning receiver/processor is used with a differential GPS (d-GPS) system. In one embodiment, the position information supplied by the altimeter is used with the motion classification algorithm to determine the type of motion being performed. Other input to the system can include human input through landmark identification, and initial position input (i.e., an absolute position).

In an exemplary embodiment, a d-GPS 510 receiver/processor and an altimeter 520 are incorporated into the system 500. The d-GPS 510 allows for information to be gathered which accurately tracks the time and the position of the moving user. The use of the d-GPS 510 allows for an additional set of values for the distance traveled and position for the individual (where the other values for the position and distance traveled were derived from the inertial processing unit 430 and the motion classifier 420). The d-GPS 510 provides superior position and distance traveled data as compared to either the inertial navigation or motion classification.

The Kalman filter 440 integrates the distance-traveled estimate from the d-GPS 510 and the inertial processing unit 430. In one embodiment, the distance-traveled estimate of the two units will result in different values for the distance traveled. In this embodiment, the Kalman filter 440 treats the difference between these two estimates as a measurement. Based on this measurement, the Kalman filter 440 modifies the estimate of the inertial navigation. The Kalman filter 440 is also programmed to supply estimated motion data by taking the difference in distance estimate measurements from the motion model and the d-GPS position estimate. Based on the difference, errors in the motion model estimates (e.g., first position estimate) are identified and modifications are made to the parameters of the motion models for better estimates of position and distance traveled by the motion models. In one embodiment, changes to the motion model parameter values are specific to the human user.

Additionally, embodiments derive a heading from the d-GPS 510 position estimates when an individual travels a sufficient distance. This heading information can then be used to calibrate the magnetometer. This information can also be used with the heading values from the magnetic sensors and the inertial processing unit 430 to provide the blended heading solution as previously described to give the best estimate of the heading using all available devices. The distance traveled and the position of the human is then displayed in a human perceptible form on the output terminal 460.

An exemplary system consists of a Honeywell Miniature Flight Management Unit (MFMU), a Watson Industries magnetometer/inertial measurement unit (IMU) (1–2° heading accuracy), a Honeywell BG1237 air pressure transducer, and a Trimble DGPS base station. The MFMU include a Honeywell HG1700 ring laser gyroscope (RLG)-based IMU (1°/hr gyro bias, 1 mg acceleration bias) and a Trimble DGPS-capable Force 5 C/A-code GPS receiver. These components were mounted on a backpack that was relatively rigid when properly strapped on.

The following is an overview of the processing flow and highlights of the special processing features being done in the navigation with the integrated Kalman filter.

Kalman Filter Definition

The exemplary Kalman filter is implemented with 27 error states. Specifically, $$sv=[\Delta p_x, \Delta p_y, \Delta p_z, \Delta v_x, \Delta v_y, \Delta v_z, \psi_x, \psi_y, \psi_z, gb_x, gb_y, gb_z, ab_x, ab_y, ab_z, f_{gps}, p_{gps}, hb_{baro}, ds, dl, daz, del, eb, es1, ec1, es2, ec2]^T$$

where $\Delta p_x$, $\Delta p_y$, $\Delta p_z$=horizontal position errors in local level frame $\Delta v_x$, $\Delta v_y$, $\Delta v_y$=horizontal velocity errors in local level frame $\psi_x$, $\psi_y$, $\psi_z$=attitude error in the local level frame $gb_i$=uncalibrated gyro biases $ab_i$=uncalibrated accelerometer biases $f_{gps}$=GPS clock frequency error $p_{gps}$=GPS clock phase error $hb_{baro}$=Barometric altimeter bias error ds=Step model slope error dl=Step model length error daz=Step model azimuth boresight error del=Step model elevation boresight error eb=magnetometer bias error es1=magnetometer one cycle sine error ec1=magnetometer one cycle cosine error es2=magnetometer two cycle sine error ec2=magnetometer two cycle cosine error The measurements for the exemplary Kalman filter include up to 8 GPS pseudo ranges, a baro altimeter altitude, three components of the step length distance and the magnetometer heading. Since the Kalman is implemented with error states, these measurements are all computed as errors from the inertial navigation solution. The measurement vector is written in the following form:

$$y=[\Delta p_1 \Delta p_2 \ldots \Delta p_1 \Delta h_b \Delta px_{mc} \Delta py_{mc} \Delta pz_{mc} \Delta_{\psi mag}]^T$$

The GPS/INS integration filter, which forms the basis of this application, has been implemented many times and will not be elaborated on here. Rather just the extensions for barometric altimeter motion classification and magnetometer aiding will be described.

Barometric Altimeter Aiding

There is one Kalman state for the altimeter aiding, the altimeter bias, which is treated as a random constant.

$$sv(18)=\text{altimeter\_bias (initial value=0.0 feet)}$$

The initial covariance for this state is:

$$P0(18,18)=2.7e6 \text{feet}^2$$

The corresponding state transition matrix element and plant covariance term are:

$$\phi(18,18)=1.$$

$$q(18,18)=10.\text{feet}^2$$

The necessary elements in the measurement matrix, h, are simply $$h(i,3)=1.$$

$$h(i,18)=1.$$

And the measurement error covariance is:

$$r(i,i)=9.0 \text{ feet}^2$$

The index, i, is used to indicate the measurement number in the measurement array, since the number of measurements is a variable.

Motion Classification Aiding

There are four Kalman filter states associated with Motion Classification, a slope for the step length model, a zero velocity step length for the model and azimuth and elevation boresight errors between the nominal stepping direction and the X axis of the inertial sensor assembly. Embodiments that classify additional motions, such as walking backward, walking sideways, or running, may require additional filter states. However, the exemplary embodiment has four states for "normal" walking.

The states for the basic motion classification (MC) model are:

$sv(19)=mc\_slope\_error$ (initial value=0.27 seconds)

$sv(j20)=mc\_length0\_error$ (initial value=1.4 feet)

$sv(21)=mc\_azimuth\text{-}boresight\_error$ (initial value=0.0 radians)

$sv(22)=mc\_elevation\_boresight\_error$ (initial value=0.0 radians)

The initial covariances for these states are:

$P0(19,19)=0.0025\ sec^2$ $P0(20,20)=0.09\ feet^2$ $P0(21,21)=0.0025\ radians^2$ $P0(22,22)=0.0025\ radians^2$ The corresponding state transition matrix elements and plant covariance terms, assuming a random-walk error model, are $\phi(19,19)=1.$ $\phi(20,20)=1.$ $\phi(21,21)=1.$ $\phi(22,22)=1.$ $q(19,19)=\sigma^2_{rw,19}$ $q(20,20)=\sigma^2_{rw,20}$ $q(21,21)=\sigma^2_{rw,21}$ $q(22,22)=\sigma^2_{rw,22}$ where $\sigma_{rw}$=random spectral intensity (0.001 used for all terms)

The equation that describes the Motion Classification (MC) measurement for the Kahnan filter is:

$$z=\delta D^{v+\psi\times\delta P}{}_n^v - C\delta d_{mc}^b + \eta$$

where z=measurement vector (3×1)

$\delta D^v$=position error vector in local vertical frame $\psi$=attitude error vector $\delta P_n^v$=delta position since last measurement in local vertical frame C=body to local vertical transformation matrix $\delta d_{mc}^b$=Motion Classification error vector in body coordinates $\eta$=white noise on position measurements The equation for step distance in terms of the time period of the step is also required for the definition of the Kalman filter.

$$di = \frac{l_0 dt_s}{dt_s - S}$$

where $l_0$ and S are step models parameters, unique for each individual $dt_S$ is the time period of the step Typically, several steps will occur during one Kalman period, $dt_{kf}$, therefore the total step distance during that period is approximated by $$dl_{kf} = \frac{l_0 dt_{kf}}{dt_{ave} - S}$$

where $dt_{ave}$ is the average period of the steps during the last Kalman period.

From these equations the h matrix for the measurement model are defined. In one embodiment, the dimension of the matrix is variable, where a maximum matrix dimension is 13×27. The local vertical navigation position change components since the last measurements are [dx1, dy1, dz1]. The indices for these measurements are designated k, k+1 and k+2. Then $dxb=C(1,1)dx1+C(2,1)dy1+C(3,1)dz1$ $h(k,4)=dt_{kf}$ $h(k,8)=dz1$ $h(k,9)=-dy1$ $h(k,19)=-C(1,1)*l_0*dt_{kf}/(dt_{ave}-S)^2$ $h(k,20)=-C(2,1)*dt_{kf}/(dt_{ave}-S)$ $h(k,21)=-C(2,2)*dxb$ $h(k,22)=C(1,3)*dxb$ $h(k+1,5)=dt_{kf}$ $h(k+1,7)=-dz1$ $h(k+1,9)=dx1$ $h(k+1,19)=-C(2,1)*l_0*dt_{kf}/(dt_{ave}-S)$ $h(k+21,20)=-C(2,1)*dt_{kf}/(dt_{ave}-S)$ $h(k+2,21)=-C(2,2)*dxb$ $h(k+1,22)=C(2,3)*dxb$ $h(k+2,6)=dt_{kf}$ $h(k+2,4)=dy1$ $h(k+2,2)=-dx1$ $h(k+2,19)=-C(3,1)*l_0*dt_{kf}/(dt_{ave}-S)^2$ $h(k+2,20)=-C(3,1)*dt_{kf}/(dt_{ave}-S)$ $h(k+2,21)=-C(3,2)*dxb$ $h(k+2,22)=C(3,3)*dxb$ The measurement covariance terms used for the step distance inputs are:

$r(k,k)=0.09\ feet^2$ $r(k+1,k+1)=0.09\ feet^2$ $r(k+2,k+2)=0.09\ feet^2$

To avoid causing inappropriate changes to the step model parameters, columns 19 through 22 of the h matrix are set to zero if the class of motion is not determined to be "walking" or if GPS or some other external position aid is not available.

Magnetometer Aiding

One exemplary error model for a magnetometer is hdg_error=$eb+es1 \sin(hdg)+ec1 \cos(hdg)+es2 \sin(2*hdg)+ec2 \cos(2*hdg)$ where hdg is the navigation heading and eb, es1, ec1, es2, ec2 are constants, with eb=bias offset
es1,ec1=one cycle errors
es2,ec2=two cycle errors.

The Kalman filter estimates each of these random constants in the error equation using the following state variables:

$sv(23)=eb$ (initial value=0.0)

$sv(24)=es1$ (initial value=0.0)

$sv(25)=ec1$ (initial value=0.0)

$sv(26)=es2$ (initial value=0.0)

$sv(27)=ec2$ (initial value=0.0)

The initial covariances for these states are:

$P0(23,23)=9.$ degree$^2$ $P0(24,24)=9.$ degree$^2$ $P0(25,25)=9.$ degree$^2$ $P0(26,26)=9.$ degree$^2$ $P0(27,27)=9.$ degree$^2$ The corresponding state transition matrix elements and plant covariance terms are:

$(23,23)=1.$ $(24,24)=1.$ $(25,25)=1.$ $(26,26)=1.$ $(27,27)=1.$ $q(23,23)=0.01$degree$^2$ $q(24,24)=0.01$degree$^2$ $q(25,25)=0.01$degree$^2$ $q(26,26)=0.01$degree$^2$ $q(27,27)=0.01$degree$^2$ Based on the problem geometry and the heading error equation given above, the measurement matrix elements are defined below assuming the magnetometer measurement is the nth measurement.

$h(n,7)=-\cos(hdg) \tan(pitch)$ $h(n,8)=-\sin(hdg) \tan(pitch)$ $h(n,9)=-1.0$ $h(n,23)=-1.0$ $h(n,24)=-\sin(hdg)$ $h(n,25)=-\cos(hdg)$ $h(n,26)=-\sin(2*hdg)$ $h(n,27)=-\cos(2*hdg)$ where hdg and pitch are the heading and pitch from navigation in radians.

The measurement variance used is $r(n,n)=9.0$ degree$^2$

Error Resets

At the end of each cycle of the Kalman processing, the error state variables estimated for the barometric altimeter, the magnetometer, the step model and the navigation parameters are applied to the appropriate correction terms. The state variables are then reset to zero for the start of the next Kalman cycle. The barometric error state is summed into an accumulated bias correction that is applied to each barometric altitude output. The magnetometer error states are summed into the corresponding coefficients of the heading error equation. This error equation is evaluated for each heading output and the result applied as a correction to the measured heading. The error states for the step model are summed into previous values used for the slope and minimum length parameters used in the step equation. At the start of processing these two parameters are set to nominal values.

The exemplary embodiments described herein can be incorporated into a portable unit, which is carried or worn by the user. For example, each of the components can be incorporated into a backpack or similar type structure, which can be strapped to the user with one or more straps, belts, or fasteners (e.g., hook and loop type fasteners). Alternatively, the components of the present invention can be integrated into a single unit, which is worn around the waist or arm of the user. In addition, the executable portions of the present invention can be stored on and read from read/writeable storage medium, including a magnetic, optical or electronic storage medium. In addition, it is understood that the calculation functions of the present subject matter may be executed either as firmware in a microprocessor and/or in separate specifically designed circuitry.

Figure 6:
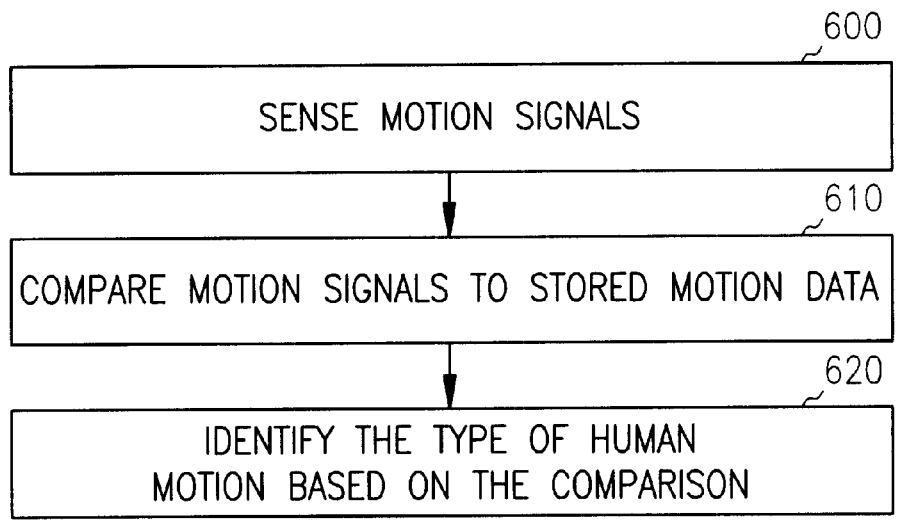
FIG. 6 shows an exemplary method of the present invention.

The present invention also includes a method of classifying human motion. In one embodiment, the classified human motion is used in conjunction with motion models specific for the type of motion identified to provide first position estimates. FIG. 6 shows an example of the method of classifying human motion. At 600, one or more motion signals are sensed. In one example, the motion signals are sensed from inertial gyroscopes and accelerometers. At 610, the motion signals are then compared to stored motion data. In one embodiment, the stored motion data includes predetermined maps of classified human motion. The classes of human motion that can be identified include walking forward, walking backwards, running, walking down or up an incline, walking up or down stairs, walking sideways, crawling, turning left, turning right, stationary, or unclassifiable. This list of motion type is exemplary and not limiting. Other motion types are known and considered within the present invention. At 620, the type of human motion is then identified based on the comparison of the motion signals to stored motion data.

In one example, comparing the signals to the stored motion data is executed in a neural network, where one or more neurons of the motion signals are generated and compared to neurons of the stored motion data of classified human motion. The type of motion is then identified as the neuron of classified human motion neuron having the smallest difference (closest fit) to the neuron generated from the signals.

Figure 7:
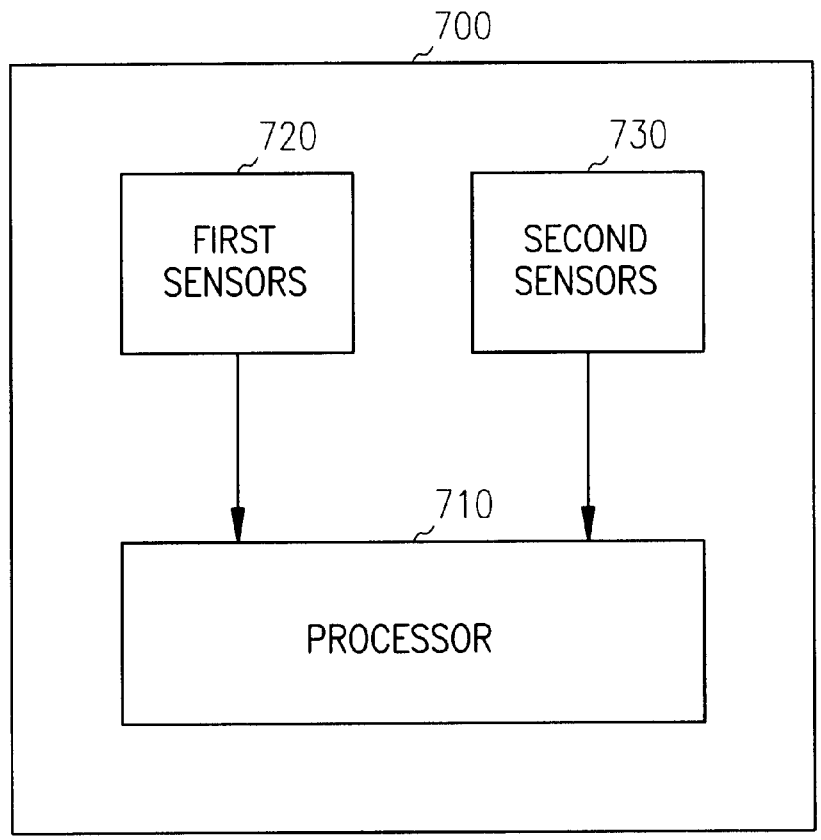
FIG. 7 shows a system of the present invention.
Figure 8A:
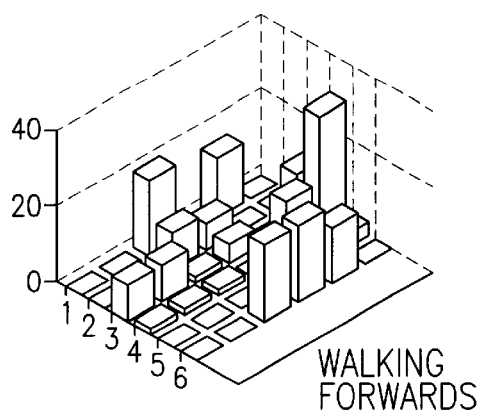
FIG. 8 shows plots of neurons representing different types of human motion.
Figure 8B:
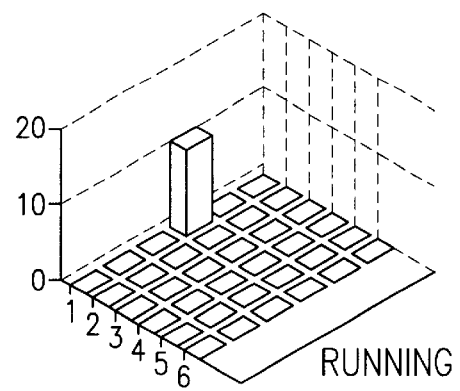
Figure 8C:
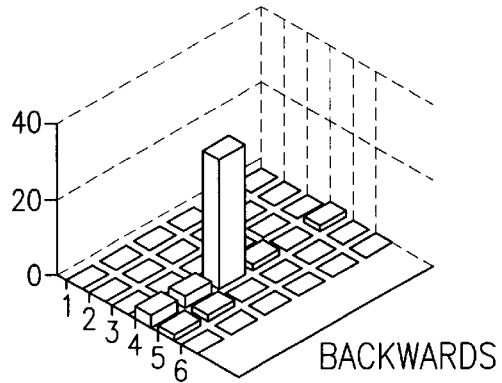
Figure 8D:
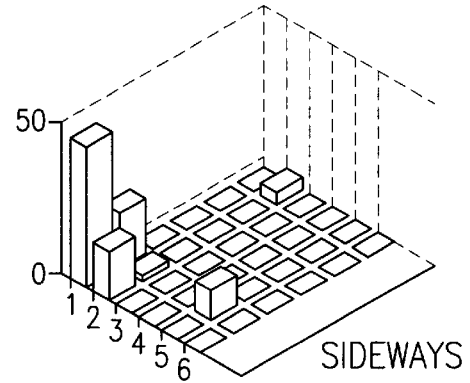
Figure 8E:
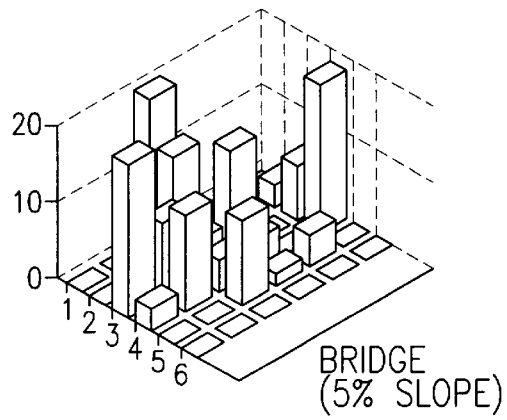
Figure 8F:
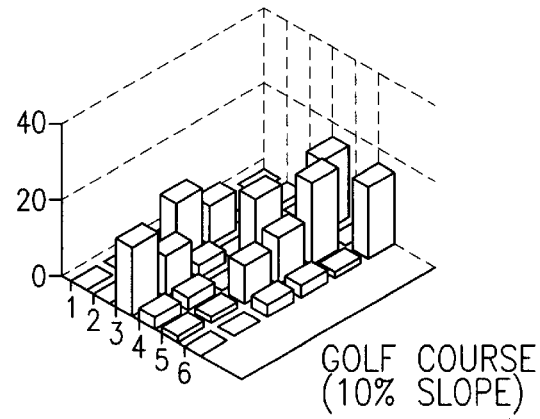
Figure 8G:
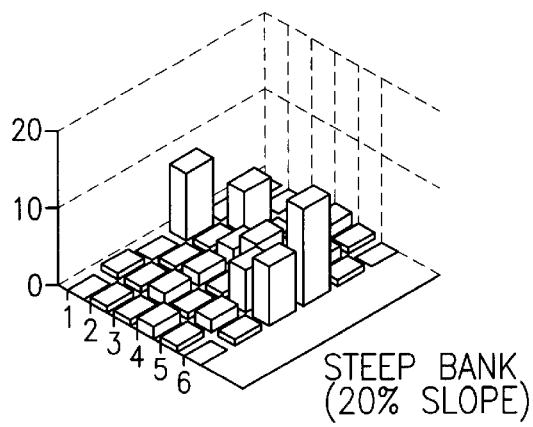
Figure 8H:
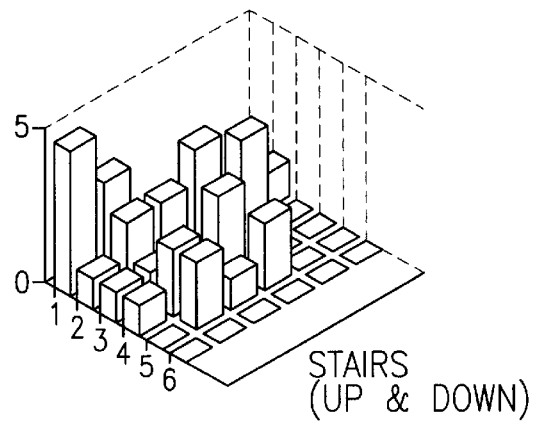
Figure 8I:
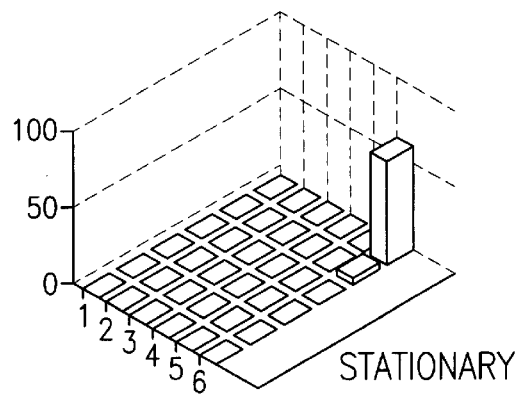
Figure 8J:
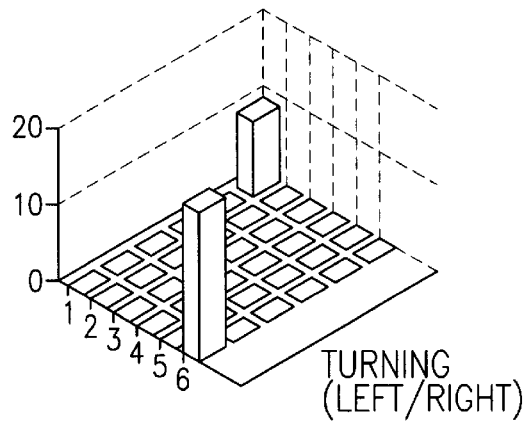
Figure 9A:
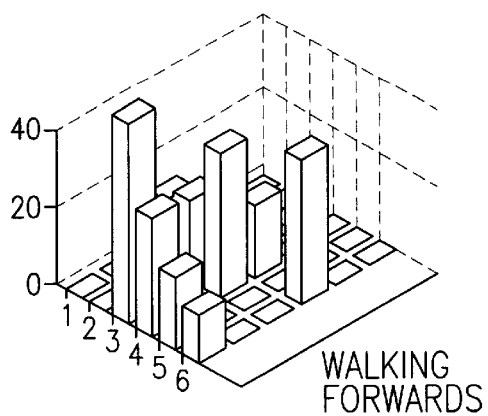
FIG. 9 shows plots of neurons representing different types of human motion.
Figure 9B:
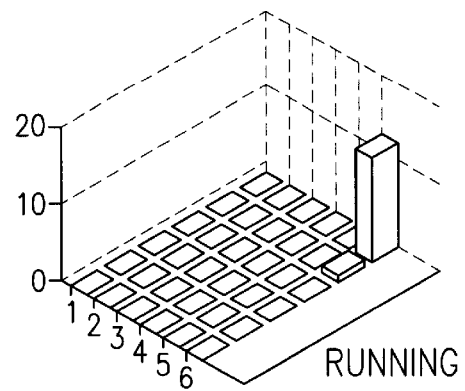
Figure 9C:
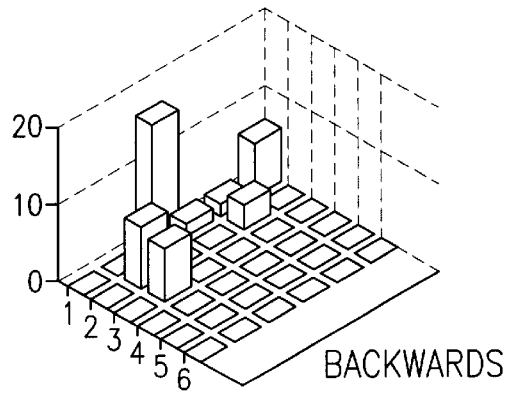
Figure 9D:
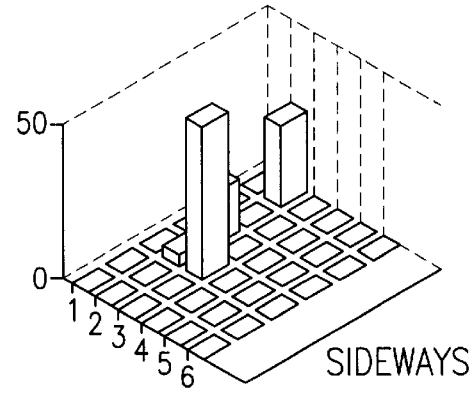
Figure 9E:
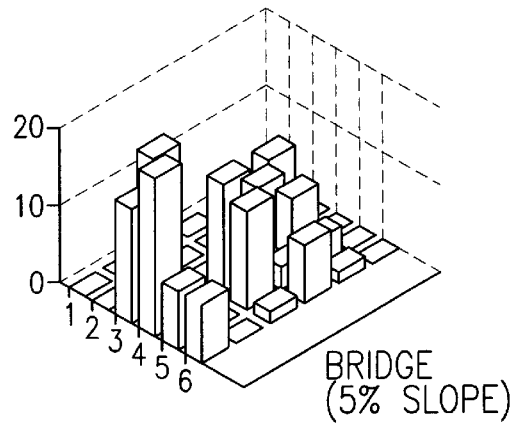
Figure 9F:
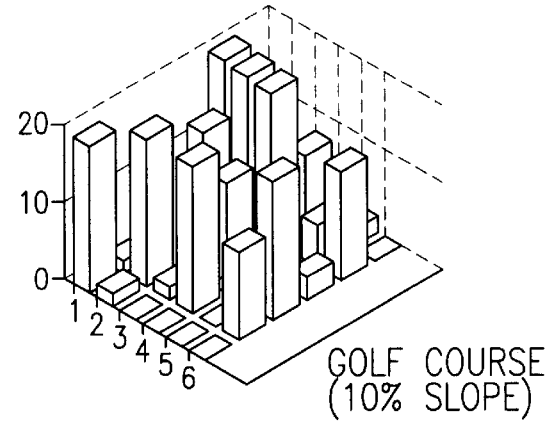
Figure 9G:
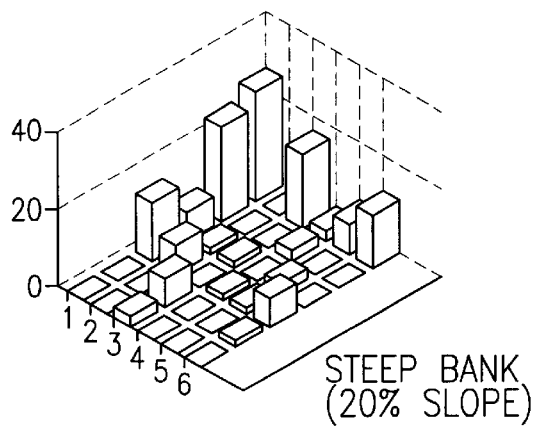
Figure 9H:
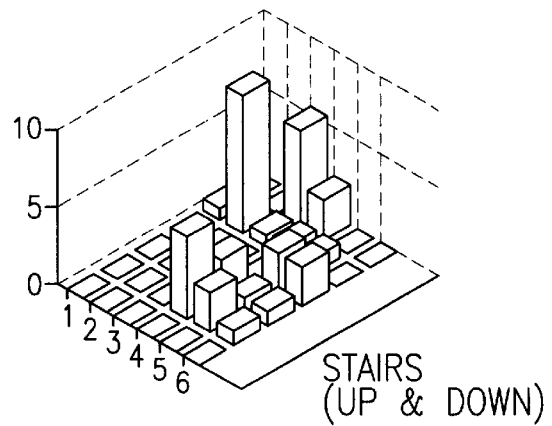
Figure 9I:
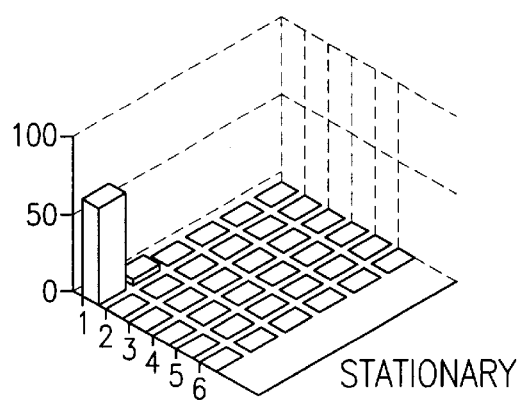
Figure 9J:
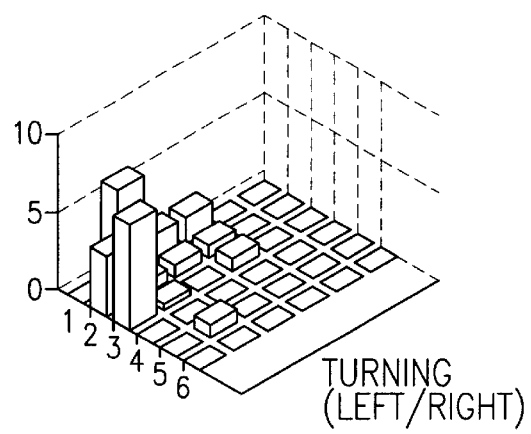

FIG. 7 shows an example of a neural network system 700. In one embodiment, the neural network system 700 is used to identify and classify different types of human motion. Once classified, motion models that are specific to the type of human motion are then used to provide first distance estimates. In one embodiment, the motion models for the different types of human motion can be executed in the motion classifier 420 to provide the first position estimate. In this example, the type of motion would first be classified. The motion model for that class of motion would then be applied and a first distance estimate determined. The Kalman filter 440 would also be used to provide feedback corrections to the motion models to provide user specific motion model corrections.

The neural network system 700 includes a processor 710 to which is coupled first sensors 720 and second sensors 730. The first sensors 720 provide a first type of motion information and the second sensors 730 provide a second type of motion information. In an exemplary embodiment, the first sensors 720 are a triad of inertial gyroscopes and the second sensors 730 are a triad of accelerometers. The first and second sensors are attached to the user and measure the angular acceleration and linear accelerations along an X-axis (defined as a forward direction perpendicular to the body plane), a Y-axis (defined as sideward direction perpendicular to the X-axis) and a Z-axis (defined as the direction perpendicular to X and Y axes). The processor 710 digitizes the time-series signals from the six sensors for the sensed motion. The time-series signals are divided into 2.56-second signal segments that correspond to 256 data points on which Fast Fourier Transform (FFT) computation is performed. Data analysis and classification are based on the information embedded in each signal segment (6 signal slices for the 6 sensors in each segment). The processor 710 then uses the first and second types of motion information to identify a type of human motion.

In one embodiment, a Self-Organizing Map (SOM) neural network is utilized for identifying and classifying an individual's motion. For example, features extracted from the signal segment are fed into the SOM neural network for clustering analysis as well as classification. The SOM contains predetermined clusters of neurons that represent a variety of human motion types. For example, predetermined clusters of neurons can be generated that represent forward and backward walking, walking sideways, walking up or down a slope, walking up or down stairs, turning left, turning right, running, or stationary, along with other human motions.

In identifying and classifying the human motion, a motion vector is received from the first sensors 720 and the second sensors 730. The processor 710 creates one or more neurons representing the motion vector(s) and then compares the neuron representing the motion input vector to the clustered neurons representing various types of human motion. In one embodiment, the type of human motion is identified based on the neurons of the predetermined human motions which has the smallest difference with the neurons representing the motion vector.

In a more particular example, the exemplary system 700 classifies the individual's motion by first constructing samples from the sensed signals by segmenting the signals for all kinds of different motion patterns (stationary, left turn, right turn, walking on flat, walking on slope, walking up/down stairs, etc.). The samples are then reduced by low-pass filtering and features are extracted from the data. In the exemplary embodiment, this entails using a FFT to transform the original time-domain data to the frequency domain by rejecting components of the resulting power spectrum that exceed a certain cut-off frequency. The information, or the energy, of the signal is primarily concentrated in the low frequency components, and the frequency components (coefficients) higher than a cutoff frequency, $f_c$, can be ignored. The exemplary embodiment uses a cut-off frequency of 15 Hz. By providing a cut-off frequency the number of data points for each sensor is reduced from 256 to 40. The input feature vector can then be formed by keeping the lower 40 frequency coefficients for each sensor. The vector length would be 240 (40*6=240) if data from 6 sensors are put together and would be 120 if either the gyroscope data or the acceleration data were used separately (for example to avoid input scaling problems). The low-pass filtering is also helpful for suppressing high-frequency noise. Other embodiments omit filtering altogether, and use band-pass filtering, or high-pass filtering, or even adaptive filtering based on step frequency or other control variables.

The SOM neural network then clusters the dimensional data automatically by organizing the position of neurons in the input space according to the intrinsic structure of the input data. SOM is one type of neural network that can learn the clustering structure of the input data. It is a competitive learning system that behaves as an adaptive vector-quantization system. SOM involves two spaces: feature (or map) space and the input data space. The feature space $\Re_m$ (m is typically 1 or 2) is usually discretized into a finite set of values called the map (a set of coordinates where the neurons locate). Vectors $\vec{z}$ in this feature space are only allowed to take values from this set. An important requirement on this set is that distance between members of the set exists. For example, a set of regular (fixed), equally spaced points like those from m-dimensional integer lattice are used for the map, but this is not necessary. In one embodiment, fixed (integer lattice) feature locations are used. The finite set of possible values of the feature set is denoted as $\Psi = \{\vec{\Psi}_1, \vec{\Psi}_2, \ldots, \vec{\Psi}_b\}$ (for example, for a 6 by 6 2-D map, b is 36). Each element $\vec{\Psi}_j$ is the coordinate vector of neuron j. Note that the elements of the set are unique, so they can be uniquely specified either by their indexes or by their coordinates in the feature space. We will use the notation $\Psi(j)$ to indicate the element $\vec{\Psi}_j$ of the set $\Psi$. The input space $\Re^d$ (d is the dimension or length of the input vector) is where the input data vectors locate. During the training process, the position of neurons in the input space ($\vec{c}_j$, j=1, ..., b) is adjusted and controlled adaptively by the input data as well as the neighborhood function defined in the feature space.

Each neuron is then trained so that the position of the neurons in input space have been fixed. After training, the clustering result can be presented by mapping the input vectors to the SOM map (nearest-neighbor mapping with $L_2$ distance). The number at each neuron position in the map space means the number of input vectors that are mapped to this neuron location. The sharper/narrower the (empirical) distribution of the numbers for each class, the better the clustering results. This means the features extracted can be used to successfully separate different classes. The performance of the feature clustering can be viewed and evaluated by 3-D graphs.

FIG. 8 shows 3-D graphs representing a 6×6 SOM map showing the magnitude of the FFT coefficients of the gyroscope data as the input. Similarly, FIG. 9 shows 3-D graphs representing a 6×6 SOM map showing the magnitude of the FFT coefficients of the acceleration data as the input. Differences in the SOM mappings are utilized to distinguish and classify an individual's motion given an individual's motion vector. In one embodiment, the neuron that has the smallest distance from the input vector in the input space is selected and the class (properties) associated with this neuron can be used to predict the motion status of the input vector. Additional classifiers can also be used with the present subject matter. These other classifiers include, but are not limited to, K-Nearest Neighbors (KNN), Multi-Layer Perceptron (MLP), or Support Vector Machine (SVM).

With respect to the exemplary SOM neural network, two different algorithms are described. The first is a flow-through version and the second is a batch version. The flow-through version, which is particularly useful for real-time processing, uses an on-line training algorithm where individual training samples are presented one at a time. The batch version algorithm needs more memory to store all the training data at one time, but is faster. And it is more closely related to the vector quantization algorithm.

For the SOM batch algorithm, the locations of the neurons in the feature space are fixed and take values $\vec{z} \in \Psi$. The locations of the neurons in the input space $\mathfrak{R}^d$ are updated iteratively. Given training data $\vec{x}_i$, i=1, ..., n and initial centers (neuron positions in input space) $\vec{c}_j$, j=1, ..., repeat the following steps:

1. Partition

Partition the input data according to the $L_2$ distance between input vectors and neurons. For each input data point find the winning neuron:

$$\vec{z}_i = \Psi\left(\arg_j \min \|\vec{c}_j - \vec{x}_i\|^2\right), i = 1, \ldots, n$$

2. Update neuron positions

Update the positions of neurons in input space $\mathfrak{R}^d$ using the weighted average of all input data samples:

$$\vec{c}_j = \frac{\sum_{i=1}^{n} \vec{x}_i K_a(\vec{z}_j, \vec{z}_i)}{\sum_{i=1}^{n} K_a(\vec{z}_j, \vec{z}_i)}, i = 1, \ldots, n$$

where $K_a$ is a neighborhood function with width parameter a. Note the neighborhood fiction is defined in feature space rather than in input space. In one embodiment, a rectangular or Gaussian neighborhood function can be used. The function and the width decrease used are $$K_{\alpha(k)}(\vec{z}, \vec{z}') = \exp\left(-\frac{\|\vec{z} - \vec{z}'\|}{2\alpha^2(k)}\right)$$

$$\alpha(k) = \left(\alpha_{init}\left(\frac{\alpha_{final}}{\alpha_{init}}\right)\right)^{k/k_{max}}$$

where k is the iteration step and $k_{max}$ is the maximum number of iterations, which is specified by user. The initial neighborhood width $a_{init}$ is chosen so that the neighborhood covers all the neurons. The final neighborhood width $a_{final}$ controls the smoothness of the mapping and is usually chosen to cover only one neuron.

3. Decrease $\alpha$, the width of the neighborhood function and repeat for a fixed number of iterations or until the quantization error reaches some small threshold.

For the SOM flow-through (on-line) algorithm, the SOM algorithm was formulated in a flow-through fashion, where individual training samples are presented one at a time. Here the original flow-through algorithm is presented in terms of stochastic approximation. Given a discrete feature space $$\Psi = \{\vec{\Psi}_1, \vec{\Psi}_2, \ldots, \vec{\Psi}_b\}$$

data point $\vec{x}(k)$ and units $\vec{c}_j(k)$, j=1, ..., b at discrete time index k;

1. Determine the nearest ($L_2$ norm) neuron to the data point. This is called the winning neuron:

$$\vec{z}(k) = \Psi\left(\arg_j \min \|\vec{x}(k) - \vec{c}_j(k-1)\|^2\right)$$

2. Update all the neurons using the update equation:

$$\vec{c}_j(k) = \vec{c}_j(k-1) + \beta(k) K_{a(k)}(\Psi(j), \vec{z}(k))(\vec{x}(k) - \vec{c}_j(k-1)), j=1, \ldots, b$$

where the $\beta$ is learning rate and K is the neighborhood function similar to the one used in the batch algorithm. The only requirement for learning rate is that it should gradually decrease with the iteration step k. One possible exponential learning rate schedule is $$\beta(k) = \left(\beta_{init}\left(\frac{\beta_{final}}{\beta_{init}}\right)\right)^{k/k_{max}}$$

where k and $k_{max}$ is similar to the parameters used in batch algorithm. When $k_{max}$ is large or unknown, alternative schedules include $\beta(k)=1/k$ and $\beta(k)=1/((k-1)/b+1)$.

3. Decrease the learning rate and the neighborhood width and increase k=k+1.

Although the present invention has been described with reference to preferred embodiments, workers skilled in the art will recognize that changes may be made in form and detail without departing from the spirit and scope of the invention. In particular, those in the art will recognize that a signal processor could perform all the operations for implementing the invention or that multiple processors could share these operations. Of course, other changes in form and detail are also within the spirit and scope of the invention as defined in the following claims.

What is claimed is:

1. A navigation system for mounting on a human, the navigation system comprising:
   one or more motion sensors for sensing motion of the human and outputting one or more corresponding motion signals;
   first means coupled to one or more of the motion sensors to determine a first position estimate based on one or more of the corresponding signals;
   means for determining a magnetic heading and an inertial heading;
   a Kalman filter to provide correction values to the first position estimate using past and present values of the motion signals and to produce a blended heading from the magnetic heading and the inertial heading; and
   second means coupled to one or more of the motion sensors to determine a distance estimate based on one or more of the corresponding signals.

2. The system of claim 1, wherein the first and second means include at least one common motion sensor.

3. The system of claim 1, wherein the second means includes an electronic compass and the first means does not.

4. The system of claim 1, wherein the first means includes an inertial processor and the second means does not.

5. The system of claim 1, wherein the first and second means include a common processor.

6. The system of claim 1, wherein the Kalman filter respectively outputs first correction signals to the first means.

7. The system of claim 6, including an output terminal, where the output terminal displays the first position estimates in a human-perceptible form.

8. The system of claim 6, including:

means to determine a second position estimate; and means for the Kalman filter to provide corrections to the first position estimate and the distance estimate using the second position estimate.

9. The system of claim 8, including means to determine the distance estimate from a motion model.

10. The system of claim 9, including means for identifying errors in the distance estimate; and means for modifying parameters of the motion model based on the errors in the distance estimate.

11. The system of claim 1, further including means, including one or more straps, for mounting the navigation system to a portion of the human.

12. A navigation system for mounting on a human, the navigation system comprising:

one or more motion sensors for sensing motion of the human and outputting one or more corresponding motion signals;

an inertial processing unit coupled to one or more of motion sensors to determine a first position estimate and inertial heading based on one or more of the corresponding signals;

a motion classifier coupled to one or more of the motion sensors to determine a distance estimate based on one or more of the corresponding motion signals; and a Kalman filter which receives the first position estimate and the distance estimate and provides corrective feedback signals to the inertial processor for the first position estimate, wherein the Kalman filter determines the corrective feedback signals based on the first position estimate and the distance estimate and past and present values of the motion signals, and wherein the Kalman filter produces a blended heading from a magnetic heading and the inertial heading.

13. The system of claim 12, wherein the motion classifier includes magnetic sensors for determining a motion direction and uses the motion direction to determine the distance estimate.

14. The system of claim 13, where the motion classifier includes a step-distance model and uses the step-distance model to determine the distance estimate.

15. The system of claim 14, where the motion classifier uses the motion sensor to determine the frequency of steps to determine the distance estimate.

16. The system of claim 12, wherein the motion classifier classifies a user's motion as straight, turning, or unknown.

17. The system of claim 12, including a position indicator which determines a third position estimate, and where the Kalman filter provides corrections to the first position estimate and the distance estimate using the third position estimate.

18. The system of claim 17, where motion classifier uses a motion model to determine the distance estimate, and where the Kalman filter identifies errors in the distance estimate and modifies parameters of the motion model based on the errors in the distance estimate.

19. The system of claim 18, where the modified parameters are specific to one or more humans.

20. The system of claim 17, where the position indicator is a global positioning receiver/processor.

21. The system of claim 17, including an output terminal, where the output terminal displays the first position estimate in a human-perceptible form.

22. The system of claim 12, including one or more straps to mount the navigation system to a portion of the human.

23. A method of estimating foot-travel position, comprising:

providing one or more motion signals;

determining a first position estimate from the one or more motion signals;

determining a distance estimate from the one or more motion signals;

correcting the first position estimate, wherein correcting the first position estimate includes using a Kalman filter to provide corrections to the first position estimate based on past and present values of the motion signals; and blending a magnetic heading and an inertial heading to produce a blended heading using the Kalman filter.

24. The method of claim 23, where correcting the first position estimate includes using past and present values of the motion signals.

25. The method of claim 23, including displaying the first position estimate in a human-perceptible form.

26. The method of claim 23, where correcting the first position estimate includes determining a second position estimate based on past and present motion signals.

27. The method of claim 23, including determining a third position estimate from a position indicator; and determining a difference between the distance estimate and the third position estimate, where the Kalman filter uses the difference in providing corrections to the first position estimate.

28. The method of claim 27, where determining the distance estimate from the one or more motion signals includes using a motion model.

29. The method of claim 28, including determining a difference between the distance estimate and the third position estimate;

identifying errors in the distance estimate; and modifying parameters of the motion model based on the errors in the distance estimate.

* * * * *